(12) United States Patent
Akamatsu et al.

(10) Patent No.: US 10,317,540 B2
(45) Date of Patent: Jun. 11, 2019

(54) RADIATION DETECTOR AND RADIOGRAPHIC IMAGING APPARATUS

(71) Applicant: FUJIFILM Corporation, Minato-ku, Tokyo (JP)

(72) Inventors: Keiichi Akamatsu, Kanagawa (JP); Shinichi Ushikura, Kanagawa (JP); Naoto Iwakiri, Kanagawa (JP); Haruyasu Nakatsugawa, Kanagawa (JP); Naoyuki Nishino, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/903,040

(22) Filed: Feb. 23, 2018

(65) Prior Publication Data

US 2018/0275288 A1    Sep. 27, 2018

(30) Foreign Application Priority Data

Mar. 22, 2017  (JP) ................. 2017-056562

(51) Int. Cl.
| | |
|---|---|
| G01T 1/20 | (2006.01) |
| A61B 6/00 | (2006.01) |
| G01T 1/29 | (2006.01) |
| H04N 5/32 | (2006.01) |
| G01T 7/00 | (2006.01) |
| G01T 1/24 | (2006.01) |
| H05K 1/18 | (2006.01) |

(Continued)

(52) U.S. Cl.
CPC .......... *G01T 1/2006* (2013.01); *A61B 6/4233* (2013.01); *G01T 1/24* (2013.01); *G01T 1/244* (2013.01); *G01T 1/246* (2013.01); *G01T 1/2928* (2013.01); *G01T 7/00* (2013.01); *H04N 5/32* (2013.01); *H05K 1/189* (2013.01); *G01T 1/2008* (2013.01); *H05K 1/028* (2013.01); *H05K 1/147* (2013.01); *H05K 2201/10151* (2013.01)

(58) Field of Classification Search
CPC ..... G01T 1/2018; G01T 1/2006; G01T 1/244; G01T 1/2928; G01T 7/00; G01T 1/2008; G01T 1/24; G01T 1/246; H05K 2201/056; H05K 1/0216; H05K 1/189; H05K 1/028; H05K 1/147; H05K 2201/10151; A61B 6/4233; H04N 5/32
See application file for complete search history.

(56) References Cited

U.S. PATENT DOCUMENTS

2010/0072379 A1* 3/2010 Nishino ................. G01T 1/2018
250/363.08
2010/0108899 A1* 5/2010 Kobayashi .......... H01L 27/1446
250/370.09

(Continued)

FOREIGN PATENT DOCUMENTS

JP    H09-152486 A    6/1997
JP    2012-13315 A    1/2012

*Primary Examiner* — Kiho Kim
(74) *Attorney, Agent, or Firm* — Solaris Intellectual Property Group, PLLC

(57) ABSTRACT

A radiation detector includes a flexible substrate; a plurality of pixels provided on a first surface of the substrate to accumulate electrical charges generated in accordance with light converted from radiation; and a terminal region part formed with a plurality of terminal regions each including terminals connected to a predetermined pixel group including some of the plurality of pixels and formed on the first surface of the substrate.

12 Claims, 9 Drawing Sheets

(51) Int. Cl.
*H05K 1/02* (2006.01)
*H05K 1/14* (2006.01)

(56) References Cited

U.S. PATENT DOCUMENTS

2014/0321601 A1* 10/2014 Koduri .................. A61B 8/0858
378/4
2015/0131785 A1* 5/2015 Topfer .................. A61B 6/4233
378/98

* cited by examiner

RADIATION DETECTOR 10

RADIOGRAPHIC IMAGING APPARATUS 1

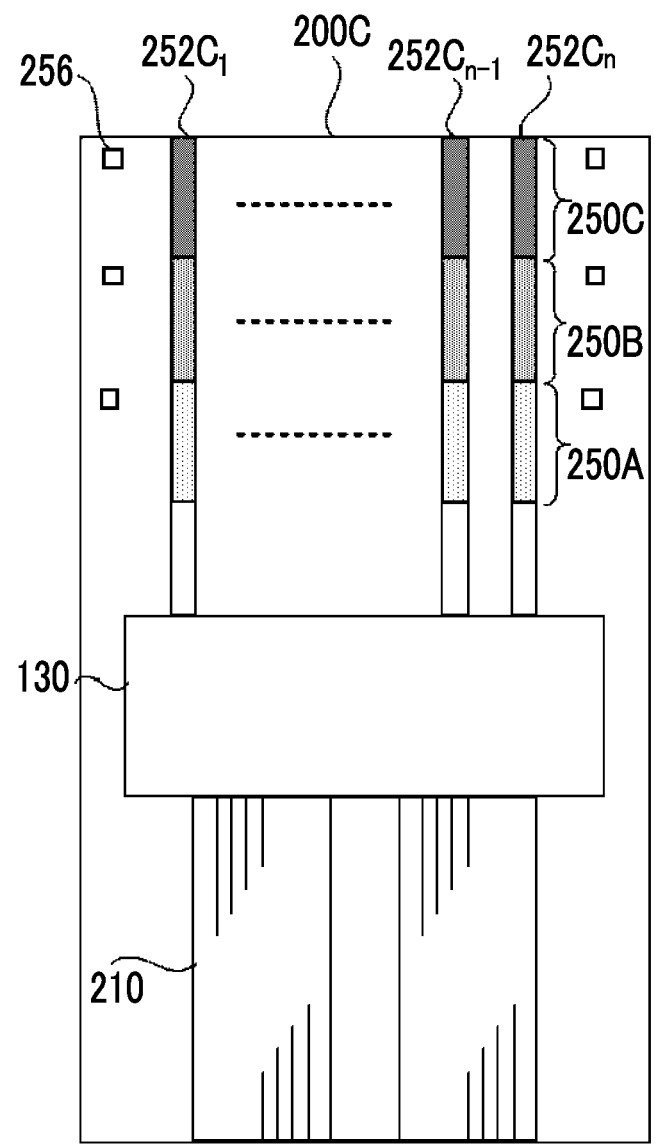

RADIATION DETECTOR AND RADIOGRAPHIC IMAGING APPARATUS

CROSS-REFERENCE TO RELATED APPLICATION

This application is based on and claims priority under 35 USC 119 from Japanese Patent Application No. 2017-056562 filed on Mar. 22, 2017, the disclosure of which is incorporated by reference herein.

BACKGROUND

Technical Field

The present invention relates to a radiation detector and a radiographic imaging apparatus.

Related Art

In the related art, radiographic imaging apparatuses that perform radiographic imaging for medical diagnosis have been known. Such radiographic imaging apparatuses include a sensor board in which a pixel group including a plurality of pixels that accumulate electrical charges generated in accordance with light converted from radiation is provided on a substrate, and a radiation detector that detects the radiation transmitted through a subject by this sensor board to generate a radiographic image is used.

In such a radiation detector, by electrically connecting circuit parts provided outside the sensor board and the pixel group provided in the sensor board together, the electrical charges accumulated in the respective pixels are read by driving of the circuit parts.

The connection between the pixel group and the circuit parts is made by electrically connecting cables, such as flexible cables, to the substrate of the sensor board.

A radiographic imaging apparatus in which the circuit parts used for the reading of the electrical charges are mounted on the cables that electrically connects the circuit parts and the pixel group together and are formed as chips on a film (COF) is known (refer to JP1997-152486A (JP-H09-152486A) and JP2012-13315A).

Generally, in a case where cables that electrically connects the circuit parts and a pixel group together are connected to the substrate of the sensor board, there is a case where so-called reworking of detaching the cables connected to the substrate of the sensor board to newly reconnect the cables is performed due to the deviation of the connecting positions of the cables, a problem of the circuit parts mounted in the case of the cables on which the circuit parts are mounted, or the like.

Meanwhile, it is desired to use a flexible substrate for the sensor board. By using the flexible substrate, for example, there is a case where the weight of the radiographic imaging apparatus (radiation detector) can be reduced and imaging of a subject becomes easy.

In a case where the substrate used for the sensor board is flexible, for example, there is a case where the reworking in the connection of the cables to the sensor board is not easily performed due to deflection of the substrate, or the like.

SUMMARY

The present disclosure provides a radiation detector and a radiographic imaging apparatus that can facilitate reworking in the connection of a cable to a substrate.

A radiation detector according to a first aspect of the present disclosure comprises a flexible substrate; a plurality of pixels provided on a first surface of the substrate to accumulate electrical charges generated in accordance with light converted from radiation; and a terminal region part formed with a plurality of terminal regions each including a terminal connected to a predetermined pixel group including some of the plurality of pixels and formed on the first surface of the substrate.

Additionally, in the radiation detector according to a second aspect of the present disclosure, the terminal region part may be provided in a region of an outer peripheral part of the substrate, and the plurality of terminal regions may be formed side by side inward from an outer edge of the substrate.

Additionally, in the radiation detector according to a third aspect of the present disclosure, arrays of the terminal included in the terminal regions adjacent to each other may deviate from each other by a half pitch.

Additionally, in the radiation detector according to a fourth aspect of the present disclosure, the terminal region part may be provided in a region of an outer peripheral part of the substrate, and the plurality of terminal regions may be formed side by side along an outer edge of the substrate.

Additionally, in the radiation detector according to a fifth aspect of the present disclosure, a cable that connects an external circuit part and the pixel group together may be connected to a plurality of terminals inward from an outer edge of the substrate.

Additionally, in the radiation detector according to a sixth aspect of the present disclosure, a portion of the substrate in which the terminal region part is provided may be disposed with respect to the other portion of the substrate via a bent part.

Additionally, in the radiation detector according to a seventh aspect of the present disclosure, the portion of the substrate in which the terminal region part is provided may be disposed on the first surface side of the substrate by the bent part.

Additionally, in the radiation detector according to an eighth aspect of the present disclosure, the portion of the substrate in which the terminal region part is provided may be disposed on a second surface side opposite to the first surface of the substrate by the bent part.

Additionally, in the radiation detector according to a ninth aspect of the present disclosure, a region, which covers other portions of the substrate by bending a portion of the substrate in which the terminal region part is provided, may be outside a region where the pixel group is provided.

Additionally, a radiation detector according to a tenth aspect of the present disclosure comprises a flexible substrate; a plurality of pixels that are provided on a first surface of the substrate to accumulate electrical charges generated in accordance with light converted from radiation; and a plurality of terminal regions provided for a predetermined pixel groups including some of the plurality of pixels.

Additionally, a radiographic imaging apparatus according to an eleventh aspect of the present disclosure comprises the radiation detector of the present disclosure; and a cable connected to the terminal of the terminal regions of the radiation detector and mounted with a circuit part to be driven in a case where the electrical charges accumulated in the plurality of pixels are read. A length of the cable from connecting parts connected to the terminal to the circuit part may be a length according to positions of the terminal regions in the substrate of the radiation detector.

According to the present disclosure, the reworking in the connection of the cable to the substrate can be facilitated.

BRIEF DESCRIPTION OF THE DRAWINGS

FIG. 6C is a plan view illustrating an example of a cable used to electrically connect the substrate to the circuit part in a case where the number of times of reworking is the second time.

DETAILED DESCRIPTION

Hereinafter, embodiments of the invention will be described in detail with reference to the drawings. In addition, the present embodiments do not limit the invention.

First Embodiment

A radiographic imaging apparatus of the present embodiment has a function of capturing a radiographic image of an object to be imaged, by detecting radiation transmitted through a subject, which is an object to be imaged, and outputting image information representing a radiographic image of the subject.

Figure 1:
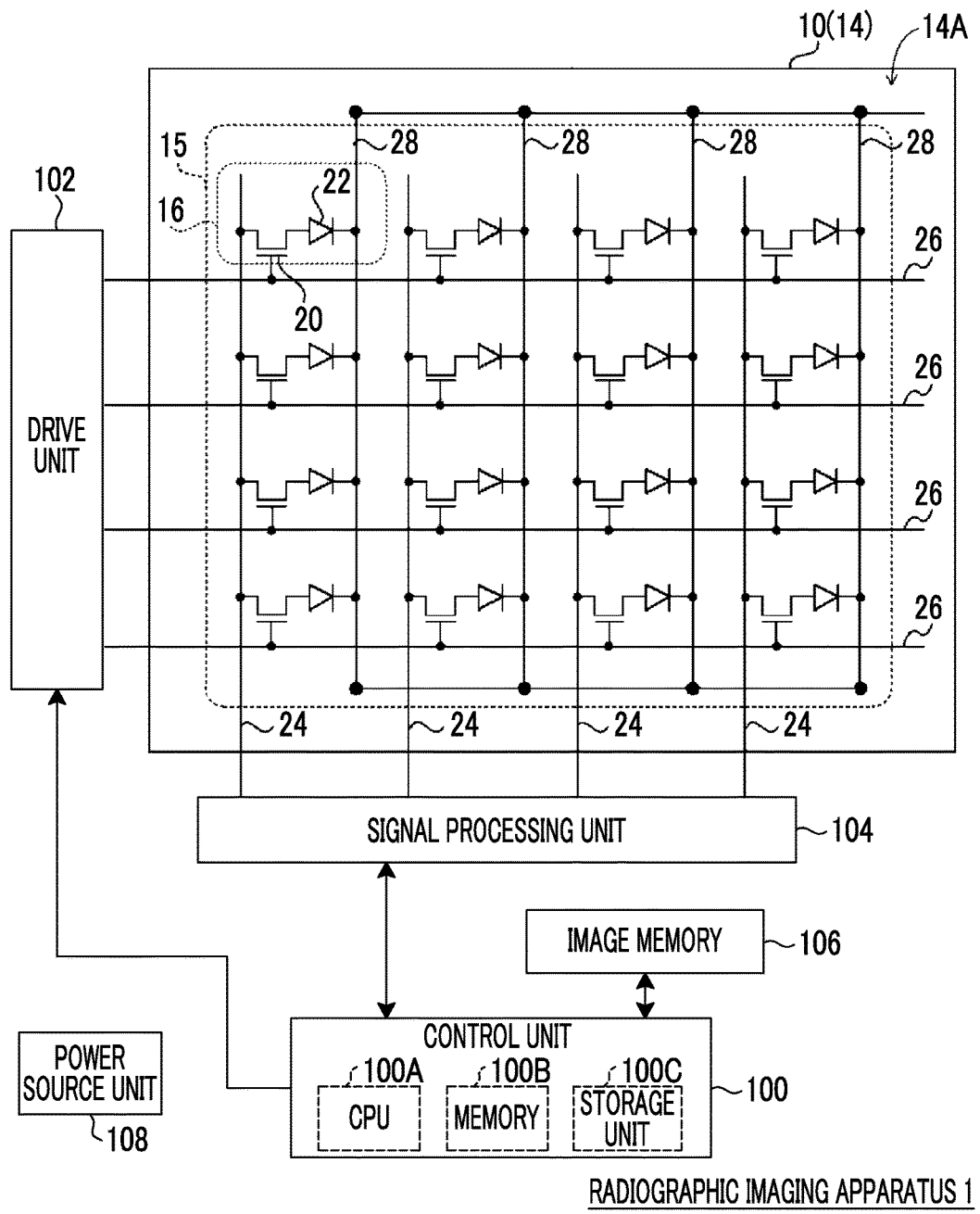
FIG. 1 is a block diagram illustrating an example of the configuration of main parts of an electrical system in a radiographic imaging apparatus of a first embodiment, and is also a configuration view illustrating an example of the configuration of a sensor board in a radiation detector.

First, the outline of an example of the configuration of an electrical system in the radiographic imaging apparatus of the present embodiment will be described with reference to FIG. 1. FIG. 1 is a block diagram illustrating an example of the configuration of main parts of the electrical system in the radiographic imaging apparatus of the present embodiment.

As illustrated in FIG. 1, the radiographic imaging apparatus 1 of the present embodiment includes a radiation detector 10, a control unit 100, a drive unit 102, a signal processing unit 104, an image memory 106, and a power source unit 108.

The radiation detector 10 includes a sensor board 12 (refer to FIG. 2) and a conversion layer (refer to FIG. 2) that converts radiation into light. The sensor board 12 includes a flexible substrate 14 and a plurality of pixels 16 provided on a first surface 14A of the substrate 14. In addition, in the following, the plurality of pixels 16 are simply referred to as "pixels 16".

As illustrated in FIG. 1, each pixel 16 of the present embodiment includes a sensor part 22 that generates and accumulates an electrical charge in accordance with the light converted by the conversion layer, and a switching element 20 that reads the electrical charge accumulated in the sensor part 22. In the present embodiment, as an example, a thin film transistor (TFT) is used as the switching element 20. For that reason, in the following, the switching element 20 is referred to as a "TFT 20". In the present embodiment, a layer in which the pixels 16 are formed on the first surface 14A of the substrate 14 is provided as a flattened layer in which the sensor parts 22 and the TFTs 20 are formed.

The pixels 16 are two-dimensionally disposed in one direction (a scanning wiring direction corresponding to a transverse direction of FIG. 1, hereinafter referred to as a "row direction"), and a direction intersecting the row direction (a signal wiring direction corresponding to the longitudinal direction of FIG. 1, hereinafter referred as a "column direction") in an active area 15 of the sensor board 12. Although an array of the pixels 16 are illustrated in a simplified manner in FIG. 1, for example, 1024×1024 pixels 16 are disposed in the row direction and the column direction.

Additionally, a plurality of scanning wiring lines 26, which are provided for respective rows of the pixels 16 to control switching states (ON and OFF) of the TFTs 20, and a plurality of signal wiring lines 24, which are provided for respective columns of the pixels 16 and from which electrical charges accumulated in the sensor parts 22 are read, are provided in a mutually intersecting manner in the radiation detector 10. The plurality of scanning wiring lines 26 are respectively connected to the drive unit 102 via terminals 52 (refer to FIG. 4), respectively, and thereby, driving signals, which are output from the drive unit 102 to drive the TFTs 20 to control the switching states thereof, flow to the plurality of scanning wiring lines 26, respectively. Additionally, the plurality of signal wiring lines 24 are respectively connected to the signal processing unit 104 via terminals 52 (refer to FIG. 4), respectively, and thereby, electrical charges read from the respective pixels 16 are output to the signal processing unit 104 as electrical signals. The signal processing unit 104 generates and outputs image data according to the input electrical signals.

The control unit 100 to be described below is connected to the signal processing unit 104, and the image data output from the signal processing unit 104 is sequentially output to the control unit 100. The image memory 106 is connected to the control unit 100, and the image data sequentially output from the signal processing unit 104 is sequentially stored in the image memory 106 under the control of the control unit 100. The image memory 106 has a storage capacity capable of storing image data equivalent to a predetermined number of sheets, and whenever radiographic images are captured, image data obtained by the capturing is sequentially stored in the image memory 106.

The control unit 100 includes a central processing unit (CPU) 100A, a memory 100B including a read only memory (ROM), a random access memory (RAM), and the like, and a nonvolatile storage unit 100C, such as a flash memory. An example of the control unit 100 is a microcomputer or the like. The control unit 100 controls the overall operation of the radiographic imaging apparatus 1.

Figure 3:
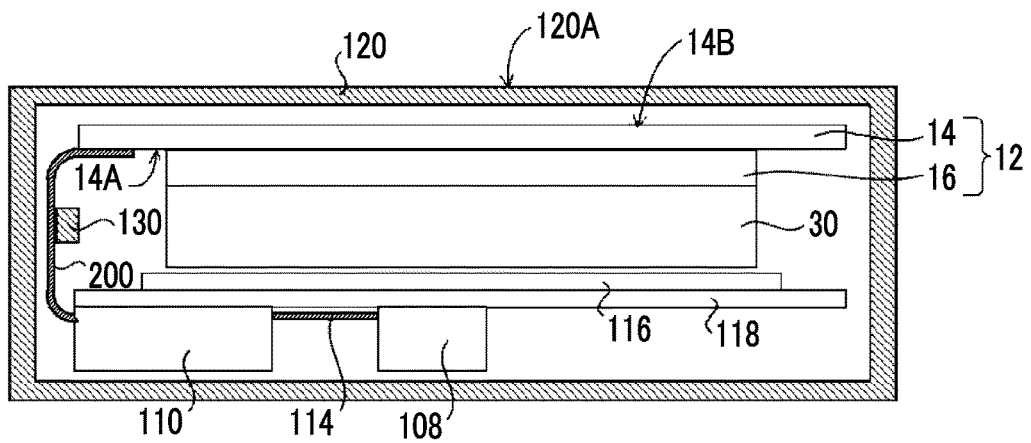
FIG. 3 is a cross-sectional view illustrating an example of a state where the radiation detector is provided within a housing in a case where the radiation detector of the first embodiment is applied to an irradiation side sampling type radiographic imaging apparatus.

In addition, in the radiographic imaging apparatus 1 of the present embodiment, the image memory 106, the control unit 100, and the like are formed in the control board 110 (refer to FIG. 3). Additionally, the respective functions of the drive unit 102 and the signal processing unit 104 are realized by a circuit part 130 (refer to FIG. 3), such as an IC that cooperates with a circuit, an element, and the like that are mounted on the control board 110. The circuit part 130, control board 110, and the pixels 16 are electrically connected together by flexible cables 200 (refer to FIG. 3) including a plurality of signal lines. In addition, although a configuration for electrically connecting the circuit part 130 and the pixels 16 will be described below, the same configuration is adopted in the drive unit 102 and the signal processing unit 104. Therefore, in the following, in the present embodiment, a circuit part for realizing the drive unit 102 and a circuit part for realizing the signal processing unit 104 are generically referred to as the "circuit part 130".

Additionally, common wiring lines 28 are provided in a wiring direction of the signal wiring lines 24 at the sensor parts 22 of the respective pixels 16 in order to apply bias voltages to the respective pixels 16. Bias voltages are applied to the respective pixels 16 from a bias power source by connecting the common wiring lines 28 to the bias power source (not illustrated) outside the sensor board 12 via a pad (not illustrated).

The power source unit 108 supplies electrical power to various elements or various circuits, such as the control unit 100, the drive unit 102, the signal processing unit 104, the image memory 106, and power source unit 108. In addition, in FIG. 3, illustration of wiring lines, which connect the power source unit 108 and various elements or various circuits together, is omitted in order to avoid complication.

Figure 2:
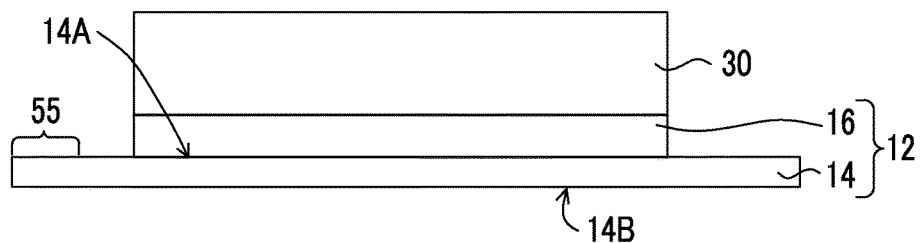
FIG. 2 is a cross-sectional view illustrating the outline of an example of the radiation detector of the first embodiment.

Moreover, the radiation detector 10 of the present embodiment will be described in detail. FIG. 2 is a cross-sectional view illustrating the outline of an example of the radiation detector 10 of the present embodiment.

As illustrated in FIGS. 2 and 3, the radiation detector 10 of the present embodiment includes the sensor board 12 including the substrate 14 and the pixels 16, and a conversion layer 30, and the substrate 14, the pixels 16, and the conversion layer 30 are provided in this order. In addition, in the following, a direction (upward-downward direction in FIG. 3) in which the substrate 14, the pixels 16, and the conversion layer 30 are arranged is referred to as a lamination direction.

The substrate 14 is a resin sheet having flexibility and including, for example, plastics, such as polyimide. A specific example of the substrate 14 is XENOMAX (registered trademark). In addition, the substrate 14 may have any desired flexibility and is not limited to the resin sheet. For example, the substrate 14 may be a relatively thin glass substrate. The thickness of the substrate 14 may be a thickness such that desired flexibility is obtained in accordance with the hardness of a material, the size of the sensor board 12 (the area of the first surface 14A or the second surface 14B), or the like. For example, in a case where the substrate 14 is the resin sheet, the thickness thereof may be 5 µm to 125 µm. Additionally, in a case where the substrate 14 is the glass substrate, the substrate 14 has flexibility in a case where the thickness thereof becomes 0.3 mm or less in a size in which one side is 43 cm or less. Therefore, the thickness may be 0.3 mm or less.

As illustrated in FIG. 2, the plurality of pixels 16 are provided in an inner partial region on the first surface 14A of the substrate 14. That is, in the sensor board 12 of the present embodiment, no pixel 16 is provided at an outer peripheral part of the first surface 14A of the substrate 14. In the present embodiment, the region on the first surface 14A of the substrate 14 where the pixels 16 are provided is used as the active area 15. In addition, in the present embodiment, as an example, the pixels 16 are provided on the first surface 14A of the substrate 14 via an undercoat layer (not illustrated) using SiN or the like.

Additionally, as illustrated in FIG. 2, a terminal region part 55 in which a plurality of terminal regions 50 including a terminal electrically connected to the signal wiring lines 24 or the scanning wiring lines 26 are formed are provided at an outer periphery of the first surface 14A of the substrate 14, and the circuit part 130 is connected to the signal wiring lines 24 or the scanning wiring lines 26 via the terminal provided in the terminal region 50 (will be described below in detail).

Additionally, as illustrated in FIG. 2, the conversion layer 30 covers the active area 15. In the present embodiment, a scintillator including CsI (cesium iodide) is used as an example of the conversion layer 30. It is preferable that such a scintillator includes, for example, CsI:Tl (cesium iodide to which thallium is added) or CsI:Na (cesium iodide to which sodium is added) having an emission spectrum of 400 nm to 700 nm at the time of X-ray irradiation. In addition, the emission peak wavelength in a visible light region of CsI:Tl is 565 nm.

In the present embodiment, the conversion layer 30 of CsI is directly formed as a columnar crystal on the sensor board 12 by a vapor-phase deposition method, such as a vacuum vapor deposition method, a sputtering method, and a chemical vapor deposition (CVD) method. In this case, the side of the conversion layer 30, which in contact with the pixels 16, becomes a base point side in a growth direction of the columnar crystal.

In addition, in this way, in a case where the conversion layer of CsI is directly formed on the sensor board 12 by the vapor-phase deposition method, for example, a reflective layer (not illustrated) having a function of reflecting the light converted in the conversion layer 30 may be provided on the surface of the conversion layer opposite to the side in contact with the sensor board 12. The reflective layer may be directly provided in the conversion layer 30, and or may be provided via an adhesion layer or the like. As a material of the reflective layer in this case, it is preferable to use an organic material, and it is preferable to use, for example, at least one of white polyethylene terephthalate (PET), $TiO_2$, $Al_2O_3$, foamed white PET, a polyester-based high-reflection sheet, specular reflection aluminum, or the like. Particularly, it is preferable to use the white PET as the material from a viewpoint of reflectivity.

In addition, the white PET is obtained by adding a white pigment, such as $TiO_2$ or barium sulfate, to PET. Additionally, the polyester-based high-reflection sheet is a sheet (film) having a multilayer structure in which a plurality of thin polyester sheets are laminated. Additionally, the foamed white PET is white PET of which the front surface is porous.

Additionally, in a case where the scintillator of CsI is used as the conversion layer 30, the conversion layer 30 can also be formed in the sensor board 12 by a method different from that of the present embodiment. For example, the conversion layer 30 may be formed in the sensor board 12 by preparing CsI vapor-deposited on an aluminum sheet or the like by the vapor-phase deposition method, and gluing the side of CsI, which is not in contact with the aluminum sheet, and the pixels 16 of the sensor board 12 together with an adhesive sheet or the like.

Moreover, unlike the radiation detector 10 of the present embodiment, GOS ($Gd_2O_2S$:Tb) or the like may be used as the conversion layer 30 instead of CsI. In this case, for example, the conversion layer 30 can be formed in the sensor board 12 by preparing a sheet glued on a support formed of the white PET or the like with an adhesion layer or the like, the sheet being obtained by dispersing GOS in a binder, such as resin, and by gluing the side of GOS on which the support is not glued, and the pixels 16 of the sensor board 12 together with an adhesive sheet or the like.

In addition, a protective film or an antistatic film that covers a part or the entirety of the radiation detector 10 or the conversion layer 30 or the like may be provided. The protective film is, for example, a PARYLENE (registered trademark) film, an insulating sheet, such as polyethylene terephthalate, or the like is used. Additionally, the antistatic film, for example, an LAPPET (registered trademark) sheet obtained by laminating aluminum, such as by bonding aluminum foil, on the insulating sheet (film), such as polyethylene terephthalate, or a film using an antistatic coating material "COLCOAT" (trade name: made by COLCOAT CO., LTD), or the like.

The radiographic imaging apparatus 1 of the present embodiment is provided within a housing through which radiation is transmitted and which has waterproofness, an antibacterial property, and sealability.

FIG. 3 is a cross-sectional view illustrating an example of a state where the radiation detector 10 is provided within a housing 120 in a case where the radiographic imaging apparatus 1 of the present embodiment is applied to an irradiation side sampling (ISS) type.

As illustrated in FIG. 3, the radiation detector 10, the power source unit 108, and a control board 110 are provided side by side in a direction intersecting the lamination direction within the housing 120. The radiation detector 10 is provided such that the second surface 14B of the substrate 14 faces an imaging surface 120A side of the housing 120 that is irradiated with radiation transmitted through a subject.

The control board 110 is a board in which the image memory 106, the control unit 100, and the like are formed, and is electrically connected to the pixels 16 of the sensor board 12 via the respective terminals 52 (refer to FIG. 4) by a plurality of cables 200 including a plurality of signal lines (signal lines 227 or the like). As illustrated in FIG. 3, the circuit part 130 connected to the signal lines within the cables 200 is mounted on the cables 200.

Additionally, the control board 110 and the power source unit 108 are connected together by a power source line 114.

A sheet 116 is further provided on a side to which the radiation transmitted through the radiation detector 10 is emitted, within the housing 120 of the radiographic imaging apparatus 1 of the present embodiment. The sheet 116 is, for example, a copper sheet. The copper sheet does not easily generate secondary radiation due to incident radiation, and therefore, has a function of preventing scattering to the rear side, that is, the conversion layer 30. In addition, it is preferable that the sheet 116 covers at least an entire surface of the conversion layer 30 side from which radiation is emitted, and covers the entire conversion layer 30 side, and it is more preferable that the sheet 116 covers the entire protective film 32. In addition, the thickness of the sheet 116 may be selected in accordance with the flexibility, weight, and the like of the entire radiographic imaging apparatus 1. For example, in a case where the sheet 116 is the copper sheet and in a case where the thickness of the sheet is about 0.1 mm or more, the sheet 116 also has a function of having flexibility and shielding secondary radiation that has entered the inside of the radiographic imaging apparatus 1 from the outside. Additionally, for example, in a case where the sheet 116 is the copper sheet, it is preferable that the thickness is 0.3 mm or less from a viewpoint of flexibility and weight.

The radiographic imaging apparatus 1 illustrated in FIG. 3 is able to capture a radiographic image in a state where the radiation detector 10 is slightly deflected in an out-plane direction of the second surface 14B of the substrate 14, for example, in a state where a central part is deflected by about 1 mm to 5 mm. For example, it is possible to maintain the radiation detector 10 in a deflected state in accordance with a capturing site or the like of a subject, and capture a radiographic image. In addition, in a case where the entire radiographic imaging apparatus 1 (radiation detector 10) is deflected and a radiographic image is captured, the influence on the image resulting from the deflection be suppressed by performing image correction.

Next, the electrical connection between the circuit part 130 and the sensor board 12 (pixels 16) in the radiographic imaging apparatus 1 of the present embodiment will be described in detail. In addition, the electrical connection by the cables 200 between the circuit part 130 for realizing the drive unit 102 and the pixels 16 and the electrical connection by the cables 200 between the circuit part 130 for realizing the signal processing unit 104 and the pixels 16 are the same. For that reason, in the following, description will be made without limiting what the circuit part 130 realizes any of the drive unit 102 and the signal processing unit 104. Additionally, for convenience of description, the signal wiring lines 24 and the scanning wiring lines 26 of description are generically referred to as "signal lines 27".

Figure 4:
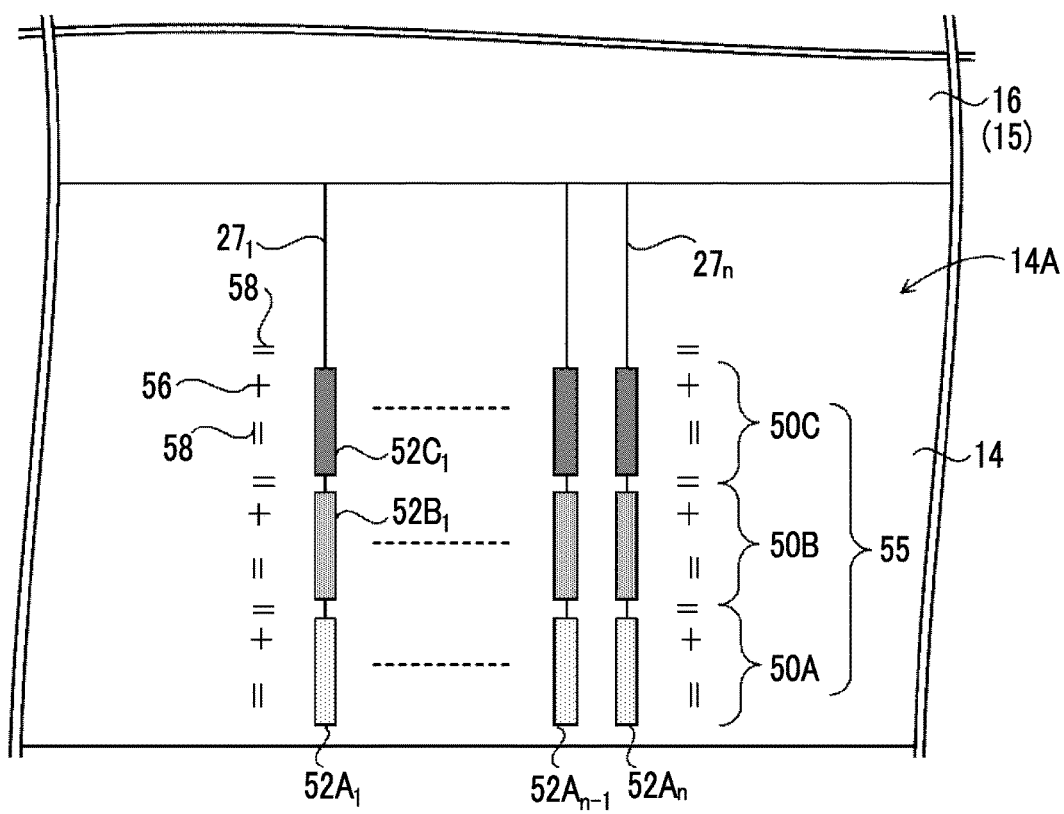
FIG. 4 is a plan view illustrating the outline of an example of terminal regions provided at an outer periphery of a substrate of a sensor board of the first embodiment.
Figure 5:
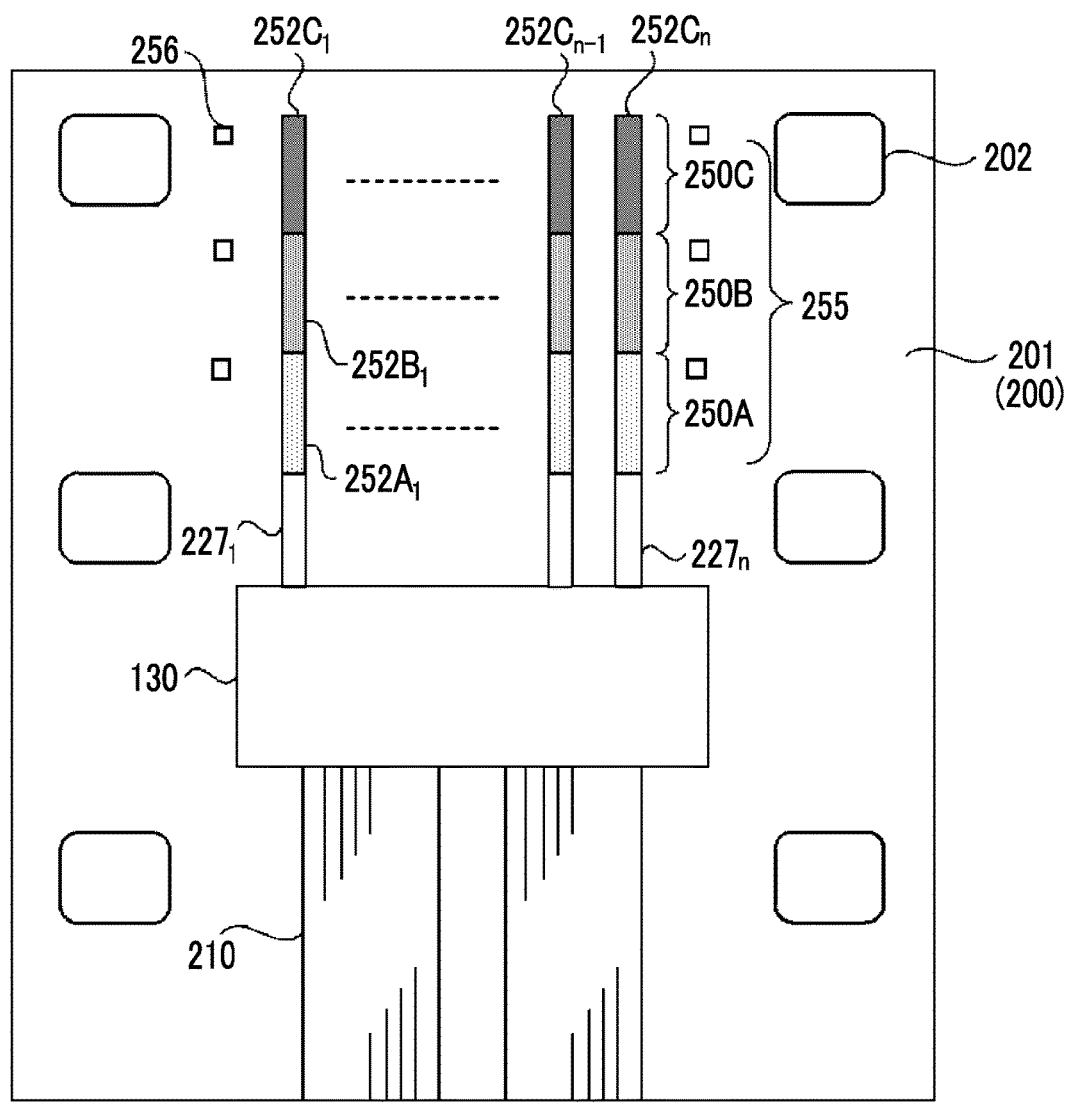
FIG. 5 is a plan view illustrating the outline of an example of a cable in a state where a circuit part in the first embodiment is mounted.

A plan view illustrating the outline of an example of the terminal region part 55 provided at the outer periphery of the substrate 14 of the sensor board 12 is illustrated in FIG. 4. Additionally, a plan view illustrating the outline of an example of a cable 200 in a state where the circuit part 130 is mounted is illustrated in FIG. 5. In addition, FIG. 5 illustrates the state of a tape reel 201 before being stamped out as the cable 200, and the cable 200 is practically obtained by stamping out the tape reel 201 as will be described below. In addition, in the present embodiment, as an example, a case where the reworking of the cable 200 can be performed twice, specifically, a case where the attachment of the cable 200 to the terminal region part 55 of the substrate 14 can be performed up to three times will be described.

In addition, in the present embodiment, detaching the cable 200 connected to the substrate 14 of the sensor board 12 to newly reconnect the cable 200 due to deviation of the connecting position of the cable 200, the problem of the mounted circuit part 130, or the like is referred to as "reworking".

Since the plurality of cables 200 are connected to the substrate 14 as described above, the radiation detector 10 of the present embodiment includes the terminal region part 55 illustrated in FIG. 4 along an outer edge of the substrate 14 for each cable 200. The terminal region part 55 includes a first terminal region 50A, a second terminal region 50B, and a third terminal region 50C as the plurality of terminal regions. In addition, in the following, in a case where the first terminal region 50A, the second terminal region 50B, and the third terminal region 50C are generically referred to without being individually distinguished from each other, these terminal regions are simply referred to as "the terminal regions 50".

In the example illustrated in FIGS. 4 and 5, the pixels 16 (signal lines 27) and the circuit part 130 are electrically connected together by connecting each of the terminals 52 (52A to 52C) provided in the substrate 14 and each of connecting parts 252 (252A to 252C) provided in the cable 200 to each other by thermocompression. In the present embodiment, a terminal 52 is provided for each signal line 27, and a case where n (n is an integer equal to or larger than 1) terminals 52 are respectively provided in the terminal regions 50 with respect to n signal lines 27 is illustrated in FIG. 4. In addition, in the present embodiment, in a case where the n terminals 52 or the n signal lines 27 are generically referred to without being individually distinguished from each other, the n terminals 52 or the n signal lines 27 are simply referred to as the "signal lines 27" or the "terminals 52", and only in a case where the n terminals 52 or the n signal lines 27 are individually distinguished from each other, the n terminals 52 or the n signal lines 27 are respectively denoted by reference signs of 1 to n to distinguish. Additionally, only in a case where the description of components corresponding to the signal lines 27 and the terminals 52 are also individually distinguished from each other, these components are similarly denoted by distinguishing reference signs of 1 to n.

In addition, a form in which, between the terminal regions 50 adjacent to each other, the terminals 52 of one terminal region 50 are respectively connected to the terminals 52 of the other terminal region 50 by thinner signal lines than the terminals 52, similar to the signal lines 27, is illustrated in FIG. 4. However, it goes without saying that wiring lines connecting the terminals 52 together between the terminal regions 50 are not limited to the form illustrated in FIG. 4. For example, a form in which the terminals 52 between the terminal regions 50 are connected together by signal lines having the same line width as each terminal 52 may be adopted.

In the terminal region part 55 provided in a region that is the outer peripheral part of the first surface 14A of the substrate 14 as illustrated in FIG. 4, the first terminal region 50A, the second terminal region 50B, and the third terminal region 50C are provided side by side inward from an outer edge of the terminal region part 55.

The first terminal region 50A is a region where terminals 52A used in a case where the cable 200 is connected to the substrate 14 for the first time (first time) is provided. As illustrated in FIG. 4, n terminals 52A are provided along the outer edge of the substrate 14 at intervals according to the wiring intervals (pitch) of the signal lines 27. Additionally, the first terminal region 50A is provided with an alignment marker 56 used for alignment in connection with the cable 200. Moreover, the first terminal region 50A s provided with a cutting marker 58 indicating a cutting position in a case where the first terminal region 50A is cut from the substrate 14.

Additionally, the second terminal region 50B is a region where terminals 52B used in a case where the cable 200 is connected to the substrate 14 for the second time, that is, in first reworking, are provided. As illustrated in FIG. 4, n terminals 52B are provided side by side with the terminals 52A at intervals according to the wiring intervals (pitch) of the signal lines 27. Additionally, the second terminal region 50B is provided with an alignment marker 56 used for alignment in connection with the cable 200. Moreover, the second terminal region 50B is provided with a cutting marker 58 indicating a cutting position in a case where the second terminal region 50B is cut from the substrate 14.

Moreover, the third terminal region 50C is a region where terminals 52C used in a case where the cable 200 is connected to the substrate 14 for the third time, that is, in second reworking, are provided. As illustrated in FIG. 4, n terminals 52C are provided side by side with the terminals 52A and the terminals 52B at intervals according to the wiring intervals (pitch) of the signal lines 27. Additionally, the third terminal region 50C is provided with an alignment marker 56 used for alignment in connection with the cable 200. Moreover, the third terminal region 50C is provided with a cutting marker 58 indicating a cutting position in a case where the third terminal region 50C is cut from the substrate 14.

Meanwhile, the cable 200 (tape reel 201) is mounted with the circuit part 130, and is provided with a plurality of signal wiring lines 210 that electrically connect the circuit part 130 and the control board 110 together. In addition, in the present embodiment, the wiring pitch of the signal wiring lines 210 is wider than the wiring pitch of the signal lines 227 (signal lines 27).

A first connection region 250A, a second connection region 250B, and a third connection region 250C are provided side by side in order from a side near the circuit part 130 in a connection region part 255 of the cable 200. In addition, in the following, in a case where the first connection region 250A, the second connection region 250B, and the third connection region 250C are generically referred to without being individually distinguished from each other, these terminal regions are simply referred to as "the connection regions 250".

The first connection region 250A is provided with n first connecting parts 252A for electrically connecting the signal lines 227 connected to the circuit part 130 to the terminals 52A. Additionally, the first connection region 250A is provided with an alignment marker 256 used in connection with the substrate 14.

Additionally, second connecting parts 252B for electrically connecting the signal lines 227 connected to the circuit part 130 to the terminals 52B are provided side by side with the first connecting parts 252A in the second connection region 250B. Additionally, the second connection region 250B is provided with an alignment marker 256 used in connection with the substrate 14.

Moreover, third connecting parts 252C for electrically connecting the signal lines 227 connected to the circuit part 130 to the terminals 52C are provided side by side with the first connecting parts 252A and the second connecting parts 252B in the third connection region 250C. Additionally, the third connection region 250C is provided with an alignment marker 256 used in connection with the substrate 14.

In the present embodiment, the number of connection regions 250 included in the cable 200 electrically connected to the substrate 14 varies in accordance with the number of times of reworking. For that reason, the cable 200 according to the number of times of reworking is formed by stamping out the tape reel 201 to a length including the connection regions 250 according to the number of times of reworking. In addition, in order to facilitate the stamping-out from the tape reel 201, it is preferable to set the intervals of the connection regions 250 to 1/N (N is an integer according to the number of connection regions 250 or the like) of the pitch of a sprocket 202.

Figure 6A:
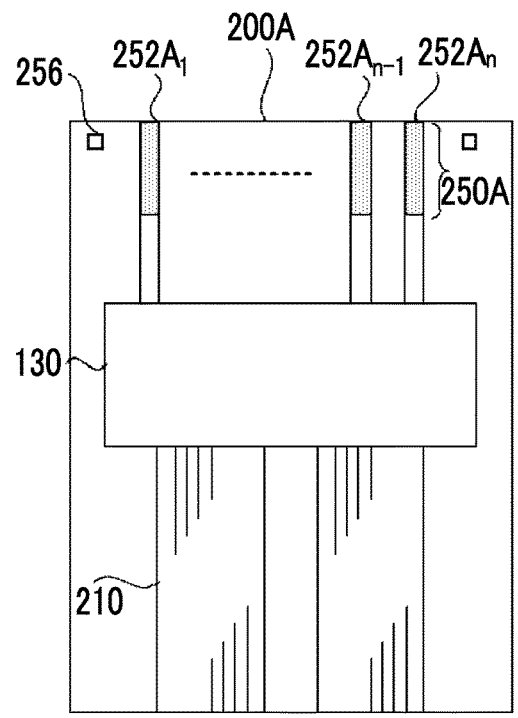
FIG. 6A is a plan view illustrating an example of a cable used to electrically connect the substrate to the circuit part in a case where the number of times of reworking is zero, that is, for the first time.
Figure 6B:
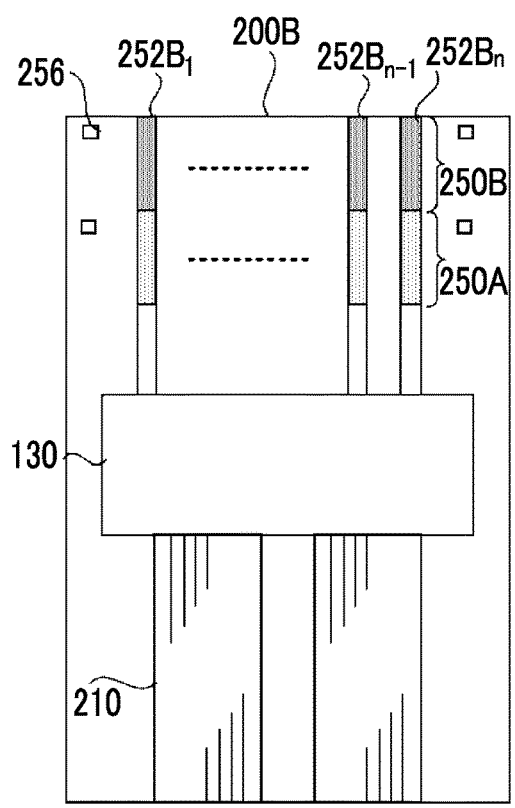
FIG. 6B is a plan view illustrating an example of a cable used to electrically connect the substrate to the circuit part in a case where the number of times of reworking is the first time.

A cable 200A, which is an example of the cable 200 used to electrically connect the substrate 14 to the circuit part 130 in a case where the number of times of reworking is zero, that is, for the first time, is illustrated in FIG. 6A. Additionally, a cable 200B, which is an example of the cable 200 used to electrically connect the substrate 14 to the circuit part 130 in a case where the number of times of reworking is the first time, is illustrated in FIG. 6B. Additionally, a cable 200C, which is an example of the cable 200 used to electrically connect the substrate 14 to the circuit part 130 in a case where the number of times of reworking is the second time, is illustrated in FIG. 6C.

As illustrated in FIG. 6A, the cable 200A is provided with only the first connection region 250A among the connection regions 250. In a case where the cable 200A is connected to the substrate 14, first connecting parts $252A_1$ to $252A_n$ of the cable 200A are respectively connected to terminals $52A_1$ and $52A_n$ of the first terminal region 50A of the substrate 14 by thermocompression.

As illustrated in FIG. 6B, the cable 200B is provided with only the first connection region 250A and the second connection region 250B among the connection regions 250. In a case the cable 200B is connected to the substrate 14, the cable 200B is connected to the substrate 14 in a state where the first terminal region 50A is cut and removed from the substrate 14. In a case where the cable 200B is connected to the substrate 14, second connecting parts $252B_1$ to $252B_n$ of the second connection region 250B of the cable 200B are respectively connected to terminals $52B_1$ to $52B_n$ of the second terminal region 50B of the substrate 14 by thermocompression.

As illustrated in FIG. 6C, all the first connection region 250A, the second connection region 250B, and the third connection region 250C among the connection regions 250 are provided in the cable 200C. In a case where the cable 200C is connected to the substrate 14, the cable 200C is connected to the substrate 14 in a state where the first terminal region 50A and the second terminal region 50B are cut and removed from the substrate 14. In a case where the cable 200C is connected to the substrate 14, third connecting parts $252C_1$ to $252C_n$ of the third connection region 250C of the cable 200C are respectively connected to terminals $52C_1$ to $52C_n$ of the third terminal region 50C of the substrate 14 by thermocompression.

In this way, in the radiation detector 10 of the present embodiment, the terminal region part 55 includes the plurality of terminal regions 50 (for example, the first terminal region 50A, the second terminal region 50B and the third terminal region 50C or the first terminal region 50A, and the second terminal region 50B). In a case where connection and reworking of the cable 200 that electrically connects the pixels 16 and the circuit part 130 together, the terminal regions 50 are sequentially used from a terminal region 50 provided at the outer edge of the substrate 14.

That is, in the radiation detector 10 of the present embodiment, in a case where the reworking is performed, the cable 200 is connected to a terminal region 50 of the substrate 14 different from a terminal region 50 of the substrate 14 from which the cable 200 is detached. Therefore, it is not necessary to take into consideration damage or the like to the respective terminals 52, the respective terminal regions 50, or the like to which the cable 200 is connected by detaching the cable 200 connected to the substrate 14 in the reworking.

Therefore, according to the radiation detector 10 of the present embodiment, the reworking in the connection of the cable 200 to the substrate 14 can be facilitated.

Additionally, in the radiation detector 10 of the present embodiment, the cables 200 to be connected to the substrate 14 are made different in accordance with to the number of times of reworking. Specifically, in the radiation detector 10 of the present embodiment, a cable 200 having a long interval from an end part of a cable 200 in which the connection regions 250 are provided to the circuit part 130 is connected as the number of times of reworking increases.

Generally, heat is generated many cases in a case where the circuit part 130 is driven. Unlike the radiation detector 10 of the present embodiment, in a case where the position of the circuit part 130 connected by the cable 200 approaches the pixels 16 (active area 15) by repeating the reworking, there is a case where the heat generated in the circuit part 130 may be transferred to the pixels 16, and image quality may be influenced, for example, such that an artifact is generated in a radiographic image. Additionally, for example, there is also a case where the generated noise may influence capturing of the radiographic image by the driving of the circuit part 130. Additionally, in a case where the position of the circuit part 130 approaches the pixels 16 (active area 15), for example, in the radiographic imaging apparatus 1 illustrated in FIG. 3, the circuit part 130 approaches the imaging surface 120A of the housing 120. Since there is concern from that the heat generated in the circuit part 130 is transferred to a subject via the housing 120 in a case where the circuit part 130 approaches the imaging surface 120A, this is not preferable.

In contrast, in the radiation detector 10 of the present embodiment, irrespective of the number of times of reworking, that is, irrespective of the position (a position from the outer edge of the substrate 14) of a connection region 250 to be connected to the cable 200, the distance between the circuit part 130 and the pixels 16 (active area 15) can be kept constant. In addition, here, the "constant" means that an error or a deviation within an allowable range is neglected and is regarded as being constant.

Therefore, according to the radiation detector 10 of the present embodiment, the deterioration of the image quality of the radiographic image as described above can be suppressed, and the transfer of heat of the circuit part 130 to the imaging surface 120A of the housing 120 can be suppressed.

Figure 7:
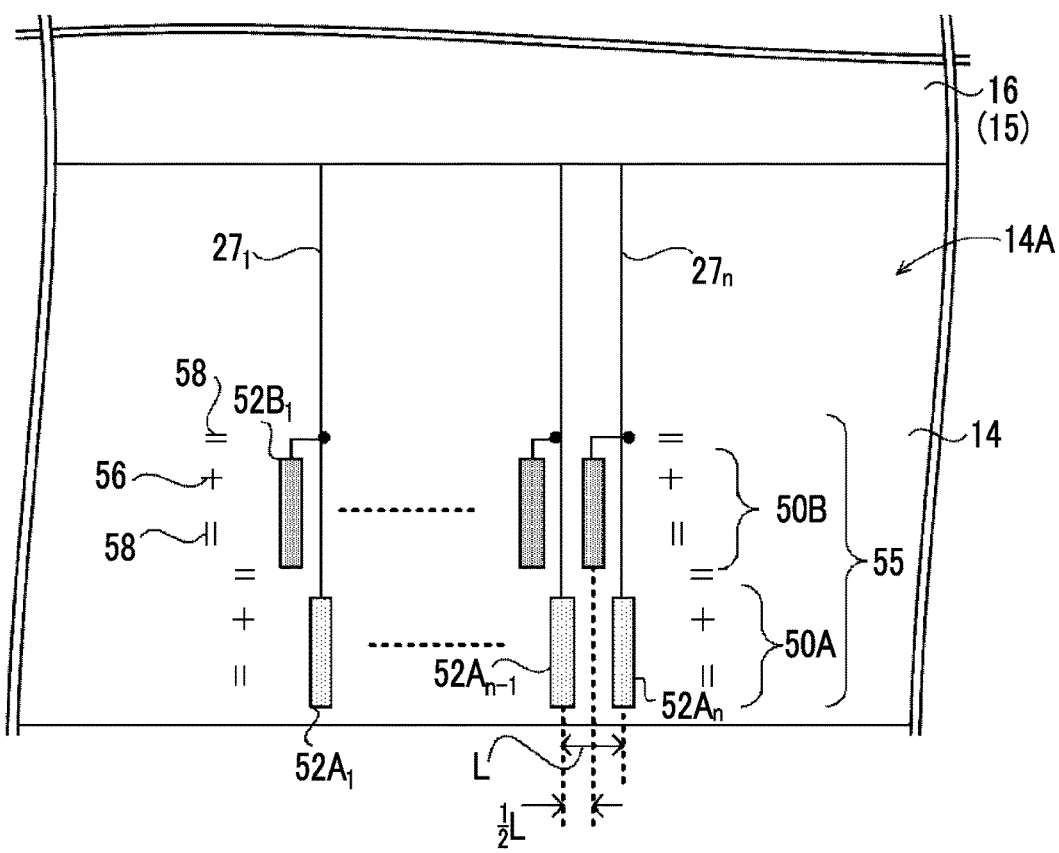
FIG. 7 is a plan view illustrating the outline of another example of the terminal regions provided at the outer periphery of the substrate of the sensor board of the first embodiment.

In addition, an example of the case where the terminal region part 55 has the plurality of terminal regions 50 inward from the outer edge of the substrate 14 is not limited to the above form illustrated in FIG. 4. For example, as illustrated in FIG. 7, the arrangement pitches of the plurality of terminals 52 that are respectively provided in the terminal regions 50 adjacent to each other may deviate from each other by a half pitch. In the form illustrated in FIG. 7, a case where the terminal region part 55 includes two terminal regions 50 of the first terminal region 50A in which the n terminals 52A are provided at an arrangement pitch L, and the second terminal region 50B in which the terminals 52B are provided at the arrangement pitch L is illustrated. In this case, as illustrated in FIG. 7, the arrangement pitches of the terminals 52A and the terminals 52B deviate from each other by a half pitch.

In this way, since the arrangement pitches of the plurality of terminals 52 that are that are respectively in the terminal regions 50 provided in the terminal region part 55 deviate from each other by a half pitch, the detachment or connection of the cable 200 from or to the substrate 14 in the reworking and connection can be facilitated.

In addition, in this way, even in a case where the arrangement pitches of the terminals 52A and the terminals 52B in the first terminal region 50A and the second terminal region 50B deviate from each other by a half pitch, the wiring pitch of the signal wiring lines 210 of the cable 200 is sufficiently wider than the wiring pitch of the signal lines 227 (signal lines 27). Therefore, the above half-pitch deviation can be absorbed.

Second Embodiment

Since a radiation detector 10 of the present embodiment is different from the first embodiment in terms of the terminal region part 55, the terminal region part 55 of the present embodiment will be described. A plan view illustrating the outline of an example of the terminal region part 55 provided at the outer periphery of the substrate 14 of the sensor board 12 in the radiation detector 10 of the present embodiment is illustrated in FIG. 8.

Figure 8:
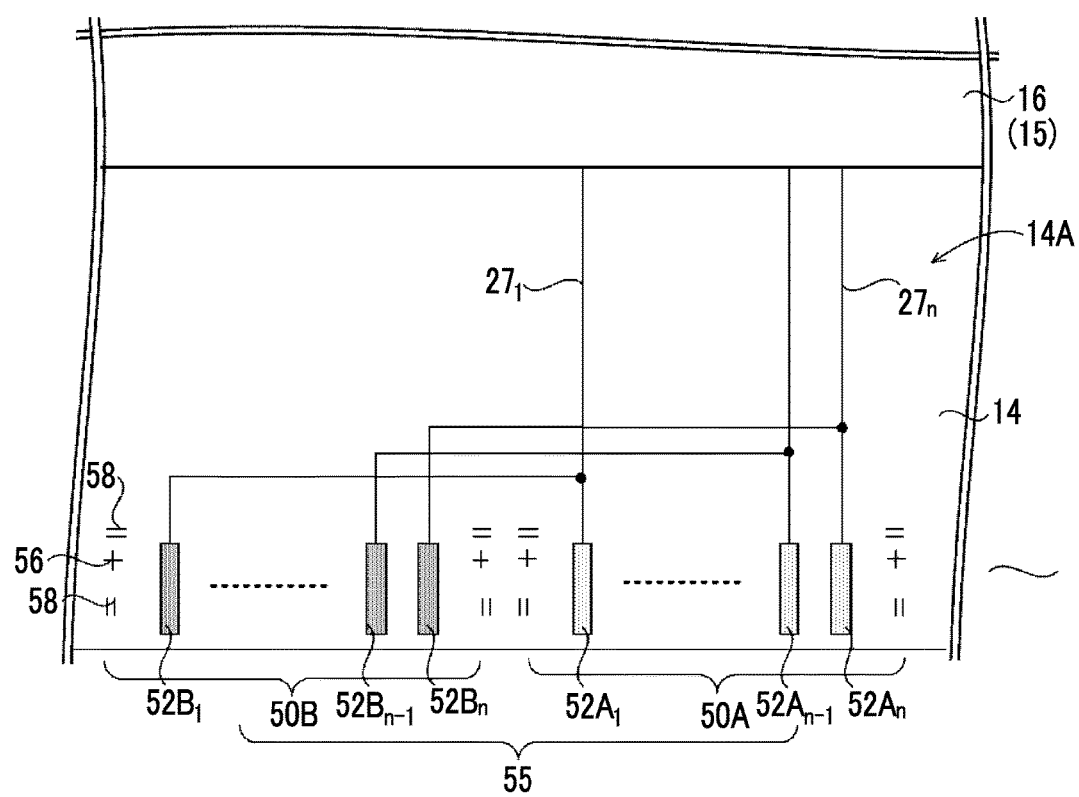
FIG. 8 is a plan view illustrating the outline of an example of terminal regions provided at an outer periphery of a substrate of a sensor board of a second embodiment.

As illustrated in FIG. 8, the terminal region part 55 of the radiation detector 10 of the present embodiment includes the first terminal region 50A and the second terminal region 50B that are aligned along the outer edge of the substrate 14.

As illustrated in FIG. 8, in a case where the first terminal region 50A and the second terminal region 50B are aligned along the outer edge of the substrate 14, even in a case where the reworking is performed unlike the radiation detector 10 of the above first embodiment, the distance from the terminals 52 to the pixels 16 (active area 15) does not change. For that reason, in the radiation detector 10 of the present embodiment, unlike the radiation detector 10 of the above first embodiment, the same cable 200, specifically, the cable 200 with the same distance from the circuit part 130 to the connecting parts 252 can be used irrespective of the number of times of reworking.

Therefore, according to the radiation detector 10 of the present embodiment, the reworking in the connection of the cable 200 to the substrate 14 can be facilitated.

As described above, the radiation detector 10 of each of the above embodiments includes the flexible substrate 14, the plurality of pixels 16 provided on the first surface 14A of the substrate 14 to accumulate the electrical charges generated in accordance with the light converted from radiation, and the terminal region part 55 formed with the plurality of terminal regions 50 each including terminals connected to a predetermined pixel group (for example, a pixel group formed by a plurality of pixels 16 connected to the same signal wiring lines 24, a pixel group formed by a plurality of pixels 16 connected to the same scanning wiring lines 26, or the like) including some of the plurality of pixels 16 and formed on the first surface 14A of the substrate 14.

Additionally, the radiographic imaging apparatus of each of the above embodiments includes the radiation detector 10, and the cable 200 connected to the terminals 52 of the terminal regions 50 of the radiation detector 10 and mounted with the circuit part 130 to be driven in a case where the electrical charges accumulated in the plurality of pixels 16 is read. The length of the cable 200 from the connecting parts 252 connected to the terminals 52 to the circuit part 130 is a length according to the positions of the terminal regions 50 in the substrate 14 of the radiation detector 10.

In the radiation detector 10 of each of the above embodiments, the substrate 14 is easily deflected. Therefore, in a case where the cable 200 is peeled from the substrate 14 for the reworking, the risk of damaging the terminal regions to which the cable 200 is connected is increased compared to a case where the substrate 14 is not deflected.

For that reason, in the radiation detector 10 of each of the above embodiments, the terminal region part 55 includes the plurality of terminal regions 50, and in a case where the reworking is performed, a cable 200 is connected to a terminal regions 50 of the substrate 14 different from a terminal region 50 of the substrate 14 from which the cable 200 is detached. Therefore, it is not necessary to take into consideration damage or the like to the respective terminals 52, the respective terminal regions 50, or the like to which the cable 200 is connected by detaching the cable 200 connected to the substrate 14 in the reworking.

Therefore, according to the radiation detector 10 of the present embodiment, the reworking in the connection of the cable 200 to the substrate 14 can be facilitated. Additionally, according to the radiation detector 10 of each of the above embodiments, a situation in which the substrate 14 or the cable 200 is damaged and becomes unusable due to the reworking can be suppressed.

In addition, in the radiation detector 10 of the above first embodiment, the terminal region part 55 provided in the substrate 14 has the plurality of terminal regions 50 inward from the outer edge of the substrate 14. Therefore, there is a case where the length from end parts of the pixels 16 (active area 15) to the outer edge becomes long at least on the sensor board 12 (substrate 14) side having the outer edge where the terminal region part 55 is provided. That is, there is a case where the width of the sensor board 12 (substrate 14) becomes large. Generally, in many cases, the radiographic imaging apparatus 1 is a so-called narrow frame having a short distance from a side surface (a surface intersecting the imaging surface 120A) of the housing 120 to an end part of the substrate 14.

Figure 9:
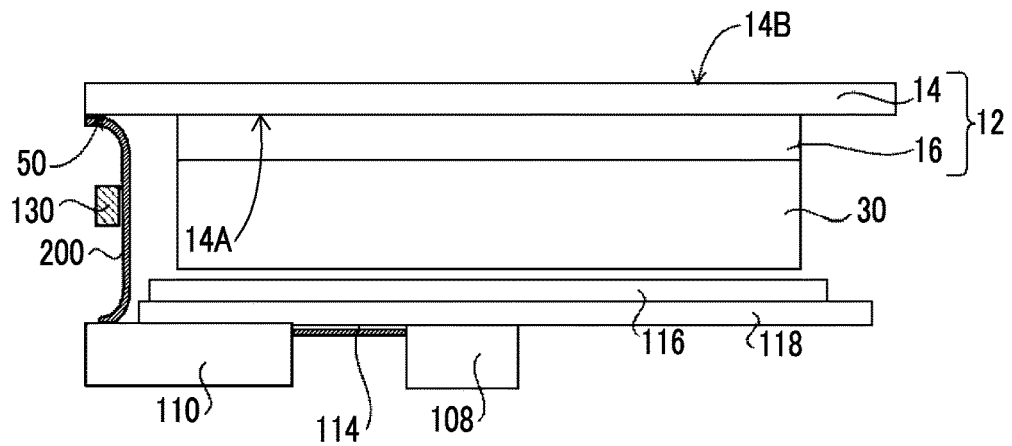
FIG. 9 is a cross-sectional view of the radiation detector for describing an example of the connection between cables and the substrate.

For that reason, in order to make the width of the entire sensor board 12 (substrate 14) in a state where the cable 200 is connected as small as possible, for example, as illustrated in FIG. 9, the cable 200 may be connected in a direction extending inward from the outer edge of the substrate 14, in a direction opposite to that in the form illustrated in FIG. 3. In other words, the cable 200 may be connected to the substrate 14 in a state where an end part of the cable 200 is directed to the end part of the substrate 14. In the form illustrated in FIG. 9, the cable 200 is connected to the substrate 14 and the control board 110 without swelling to the housing 120 side compared to the form illustrated in FIG. 3. Therefore, it is possible to suppress a situation in which the width of the entire sensor board 12 (substrate 14) in a state where the cable 200 is connected becomes large. In addition, in the form illustrated in FIG. 9, a prevention member for preventing the contact between the cable 200 and the conversion layer 30 may be provided between the cable 200 and the conversion layer 30. Additionally, by repeating the reworking, in a case where the terminal regions 50 are removed and the width of the substrate 14 becomes narrow, the cable 200 may be connected to the substrate 14 in a state where the end part of the cable 200 is directed to the active area 15 side, similarly to the form illustrated in FIG. 3 (reversely to the form illustrated in FIG. 9).

Figure 10:
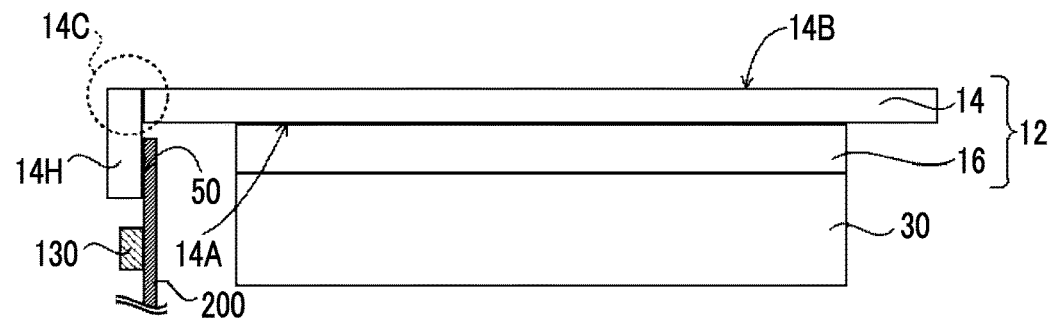
FIG. 10 is a cross-sectional view of the radiation detector for describing an example of the connection between the cables and the substrate in a case where an end part region of the substrate is bent.
Figure 11:
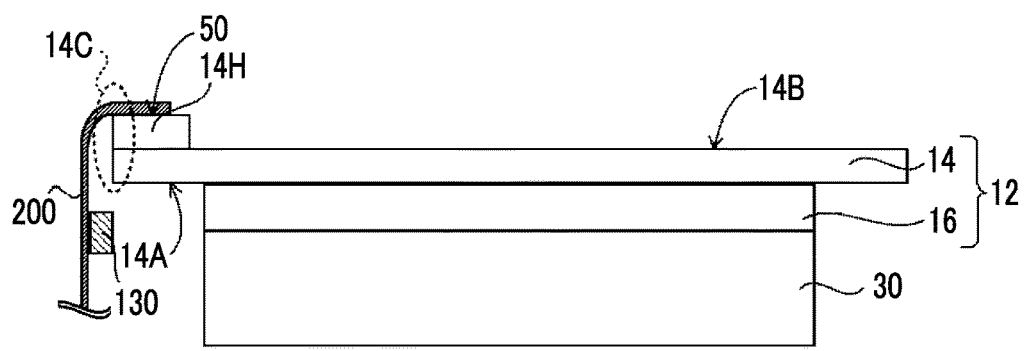
FIG. 11 is a cross-sectional view of the radiation detector for describing another example of the connection between the cables and the substrate in a case where the end part region of the substrate is bent.

Additionally, for example, the portion of the radiation detector 10 in which the terminal region part 55 of the substrate 14 is provided may be bent. For example, as illustrated in FIGS. 10 and 11, an end part region 14H of the substrate 14 in which the terminal region part 55 is provided may be disposed on other portions of the substrate 14 via a bent part 14C. An example of a state where the end part region 14H is bent toward the first surface 14A side by the bent part 14C by disposing the end part region 14H on the first surface 14A side of the substrate 14 is illustrated in a case illustrated in FIG. 10. Additionally, an example of a state where the end part region 14H is bent toward the second surface 14B side by the bent part 14C by disposing the end part region 14H on the second surface 14B side of the substrate 14 is illustrated in a case illustrated in FIG. 11. As illustrated in FIG. 11, in a case where the end part region 14H is disposed on the second surface 14B side of the substrate 14, it is preferable that the bent end part region 14H does not cover the active area 15.

Particularly, in a case where the radiation detector 10 is used for an ISS type radiographic imaging apparatus 1, it is preferable that the end part region 14H does not cover the active area 15. Additionally, in a case where the radiation detector 10 is used for the ISS type radiographic imaging apparatus 1, as illustrated in FIG. 11, it is preferable to connect the cable 200 to the end part region 14H of the substrate 14 in a state where the end part of the cable 200 is directed to an end part of the end part region 14H corresponding to the outer edge of the substrate 14. In the form illustrated in FIG. 11, the length of the cable 200 can be shortened compared to the form in which the end part region 14H is bent to the first surface 14A side, for example, in a state where the cable 200 is connected to the end part region 14H, as illustrated in FIG. 10.

In addition, in a case where the radiation detector 10 is used for a penetration side sampling (PSS) type radiographic imaging apparatus 1, the control board 110 is provided on the second surface 14B side of the substrate 14. For that reason, a distance up to the control board 110 is short even in the form in which the end part region 14H is bent to the first surface 14A side, for example, in the state where the cable 200 is connected to the end part region 14H, as illustrated in FIG. 10. Therefore, the length of the cable 200 does not become long compared to the ISS type.

Additionally, in each of the above embodiments, as illustrated in FIG. 1, an aspect in which the pixels 16 are two-dimensionally arrayed in a matrix has been described. However, the pixels 16 may be one-dimensionally arrayed or may be arrayed in a honeycomb shape. Additionally, the shape of the pixels is also not limited, and may be a rectangular shape, or may be a polygonal shape, such as a hexagonal shape. Moreover, it goes without saying that that the shape of the active area 15 is also not limited.

In addition, it goes without saying that the configurations, manufacturing methods, and the like of the radiographic imaging apparatuses 1, the radiation detectors 10, and the like that are described in the respective above embodiments are merely examples, and can be modified in accordance with situations without departing from the scope of the invention.

What is claimed is:

1. A radiation detector comprising:
a flexible substrate;
a plurality of pixels provided on a first surface of the substrate to accumulate electrical charges generated in accordance with light converted from radiation; and
a terminal region part formed with a plurality of terminal regions and formed on the first surface of the substrate, each of the plurality of terminal regions including a plurality of terminals respectively for a plurality of signal lines each connected to a predetermined pixel group including some of the plurality of pixels.

2. The radiation detector according to claim 1, wherein the terminal region part is provided in a region of an outer peripheral part of the substrate, and the plurality of terminal regions are formed side by side inward from an outer edge of the substrate.

3. The radiation detector according to claim 2, wherein arrays of the terminal included in the terminal regions adjacent to each other deviate from each other by a half pitch.

4. The radiation detector according to claim 1, wherein the terminal region part is provided in a region of an outer peripheral part of the substrate, and the plurality of terminal regions are formed side by side along an outer edge of the substrate.

5. The radiation detector according to claim 1, wherein a cable that connects an external circuit part and the pixel group together is connected to the terminal inward from an outer edge of the substrate.

6. The radiation detector according to claim 5, wherein a region, which covers other portions of the substrate by bending a portion of the substrate in which the terminal region part is provided, is outside a region where the pixel group is provided.

7. The radiation detector according to claim 1, wherein a portion of the substrate in which the terminal region part is provided is disposed with respect to the other portion of the substrate via a bent part.

8. The radiation detector according to claim 7, wherein the portion of the substrate in which the terminal region part is provided is disposed on the first surface side of the substrate by the bent part.

9. The radiation detector according to claim 7, wherein the portion of the substrate in which the terminal region part is provided is disposed on a second surface side opposite to the first surface of the substrate by the bent part.

10. A radiographic imaging apparatus comprising:
the radiation detector according to claim 1; and
a cable connected to the terminal of the terminal regions of the radiation detector and mounted with a circuit part to be driven in a case where the electrical charges accumulated in the plurality of pixels are read,
wherein a length of the cable from connecting parts connected to the terminal to the circuit part is a length according to positions of the terminal regions in the substrate of the radiation detector.

11. A radiation detector comprising:
a flexible substrate;
a plurality of pixels that are provided on a first surface of the substrate to accumulate electrical charges generated in accordance with light converted from radiation; and
a plurality of terminal regions, each of the plurality of terminal regions including a plurality of terminals respectively for a plurality of signal lines each connected to a predetermined pixel groups including some of the plurality of pixels.

12. A radiographic imaging apparatus comprising:
the radiation detector according to claim 11; and
a cable connected to the terminal of the terminal regions of the radiation detector and mounted with a circuit part to be driven in a case where the electrical charges accumulated in the plurality of pixels are read,
wherein a length of the cable from connecting parts connected to the terminal to the circuit part is a length according to positions of the terminal regions in the substrate of the radiation detector.

* * * * *